US010958646B2

(12) United States Patent
Bertrand

(10) Patent No.: US 10,958,646 B2
(45) Date of Patent: Mar. 23, 2021

(54) BIOMETRIC AUTHENTICATION WITH BODY COMMUNICATION NETWORK

(71) Applicant: Intel Corporation, Santa Clara, CA (US)

(72) Inventor: Patrice Bertrand, Tournefeuille (FR)

(73) Assignee: Intel Corporation, Santa Clara, CA (US)

( * ) Notice: Subject to any disclaimer, the term of this patent is extended or adjusted under 35 U.S.C. 154(b) by 202 days.

(21) Appl. No.: 15/774,069

(22) PCT Filed: Dec. 22, 2015

(86) PCT No.: PCT/US2015/067509
§ 371 (c)(1),
(2) Date: May 7, 2018

(87) PCT Pub. No.: WO2017/111965
PCT Pub. Date: Jun. 29, 2017

(65) Prior Publication Data
US 2018/0314858 A1 Nov. 1, 2018

(51) Int. Cl.
*H04L 29/06* (2006.01)
*A61B 5/00* (2006.01)
(Continued)

(52) U.S. Cl.
CPC ............ *H04L 63/0876* (2013.01); *A61B 5/00* (2013.01); *A61B 5/0028* (2013.01); *G06F 21/32* (2013.01);
(Continued)

(58) Field of Classification Search
CPC ....... G06F 21/64; G06F 21/32; H04B 13/005; H04B 2209/88; H04L 63/0861;
(Continued)

(56) References Cited

U.S. PATENT DOCUMENTS

2002/0109621 A1* 8/2002 Khair .................. A61B 5/0006
341/174
2009/0240131 A1 9/2009 Lu et al.
(Continued)

FOREIGN PATENT DOCUMENTS

| JP | 2008090465 A | 4/2008 |
| KR | 1020140016460 A | 2/2014 |
| WO | WO-201711965 A1 | 6/2017 |

OTHER PUBLICATIONS

"International Application Serial No. PCT/US2015/067509, International Search Report dated Sep. 6, 2016", 3 pgs.
(Continued)

*Primary Examiner* — Huan V Doan
(74) *Attorney, Agent, or Firm* — Schwegman Lundberg & Woessner, P.A.

(57) ABSTRACT

A method of authenticating a health measurement taken from a medical measurement device may include establishing a network connection between a computing device and a medical measurement device. The network connection may be established via contact of a user with electrodes of the computing device and contact of the user with electrodes of the medical measurement device. While user contact is maintained with the electrodes of the computing device, the electrodes of the medical measurement device, and a biometric sensor of the computing device health measurement data of the user may be received at the computing device from the medical measurement device. Also while contact is maintained, the user may be authenticated using a measurement of the biometric sensor of the computing device. The health measurement data may be signed based on the authenticating.

22 Claims, 6 Drawing Sheets

(51) Int. Cl.
  *H04L 9/32* (2006.01)
  *H04W 12/06* (2021.01)
  *H04W 76/10* (2018.01)
  *G06F 21/32* (2013.01)
  *G06F 21/64* (2013.01)
  *H04B 13/00* (2006.01)
  *A61B 5/117* (2016.01)

(52) U.S. Cl.
  CPC .......... *G06F 21/64* (2013.01); *H04B 13/005* (2013.01); *H04L 9/3231* (2013.01); *H04L 9/3247* (2013.01); *H04L 63/0861* (2013.01); *H04W 12/0609* (2019.01); *H04W 76/10* (2018.02); *A61B 5/0015* (2013.01); *A61B 5/117* (2013.01); *A61B 2562/08* (2013.01); *H04L 2209/88* (2013.01)

(58) Field of Classification Search
  CPC . H04L 9/3231; H04L 9/3247; H04L 63/0876; H04W 12/0609; H04W 76/10; H04W 12/06; A61B 5/00; A61B 5/0028; A61B 5/0015; A61B 5/117; A61B 2562/08
  See application file for complete search history.

(56) References Cited

U.S. PATENT DOCUMENTS

| | | | |
|---|---|---|---|
| 2011/0004072 A1* | 1/2011 | Fletcher | A61B 5/0002 600/300 |
| 2011/0161100 A1* | 6/2011 | Peak | G06Q 40/08 705/2 |
| 2012/0220835 A1* | 8/2012 | Chung | A61B 5/0022 600/301 |
| 2013/0066644 A1* | 3/2013 | Dicks | A61B 5/0022 705/2 |
| 2013/0346091 A1* | 12/2013 | Margon | G06F 19/3418 705/2 |
| 2015/0127737 A1* | 5/2015 | Thompson | G06F 19/3418 709/204 |
| 2015/0163221 A1 | 6/2015 | Bolin et al. | |
| 2015/0332031 A1* | 11/2015 | Mistry | H04W 12/06 726/19 |

OTHER PUBLICATIONS

"International Application Serial No. PCT/US2015/067509, Written Opinion dated Sep. 6, 2016", 9 pgs.

* cited by examiner

BIOMETRIC AUTHENTICATION WITH BODY COMMUNICATION NETWORK

This application is a U.S. National Stage Filing under 35 U.S.C. 371 from International Application No. PCT/US2015/067509, filed on Dec. 22, 2015, and published as WO 2017/111965 on Jun. 29, 2017, which application is incorporated herein by reference in its entirety.

BACKGROUND

Users may take health measurements using one or more devices. The devices may be worn to track a user's heart rate or count the number of steps the user takes. Other types of devices may be used to take single data points such as glucose levels. The health measurements may be transmitted to a computing device and stored for retrieval by the user.

BRIEF DESCRIPTION OF THE DRAWINGS

In the drawings, which are not necessarily drawn to scale, like numerals may describe similar components in different views. Like numerals having different letter suffixes may represent different instances of similar components. Some embodiments are illustrated by way of example, and not limitation, in the figures of the accompanying drawings in which.

DETAILED DESCRIPTION

Users increasingly have numerous devices that are capable of taking health measurement data and collect the information on a computing device (e.g., a smart phone, laptop, tablet, etc.). Throughout this disclosure, devices that have the capability of taking health measurements are referred to as medical measurement devices. A medical measurement device may take a variety of health measurement data such as SpO2, blood pressure, and blood glucose levels.

The health measurement data may be useful for many purposes, but may be difficult to verify and authenticate if not taken by a clinician or at a clinician's office. For example, a user may make measurement mistakes and a receiving system may be unable to verify that that health measurement data belongs to the submitting user. Accordingly, the technical challenge of user and device attribution may need to be overcome before a clinician may act on data provided by the user such as updating prescriptions, updating a user profile, making a diagnosis, etc.

In various examples described herein, human body communication (HBC) channels (sometimes referred to as in-body communication or IBC) and human biometrics are used to unambiguously link a user and measured health information of the user. Human body communication is a short-range non-RF wireless communication technique that uses the human body as a transmission medium (HBC has been standardized as IBC by the IEEE 802.15.6). Because the use of HBC may restrict the communication range, eavesdropping or wiretapping risks may be minimized. At the transmitting electrode of an HBC connection, the signal is modulated and flows through the body to the receiver electrode of the HBC connection, where signal variation is detected.

HBC is generally employed for data transmission in low frequency and is primarily categorized into two solutions: galvanic coupling and capacitive coupling. In the context of this disclosure, HBC is used in its galvanic coupling form. Galvanic coupling approach requires the HBC transceiver to have direct physical access to the body by having both of the transceiver's electrodes (RX, GND, TX, GND) on the body (the body acting as a transmission line).

Figure 1:
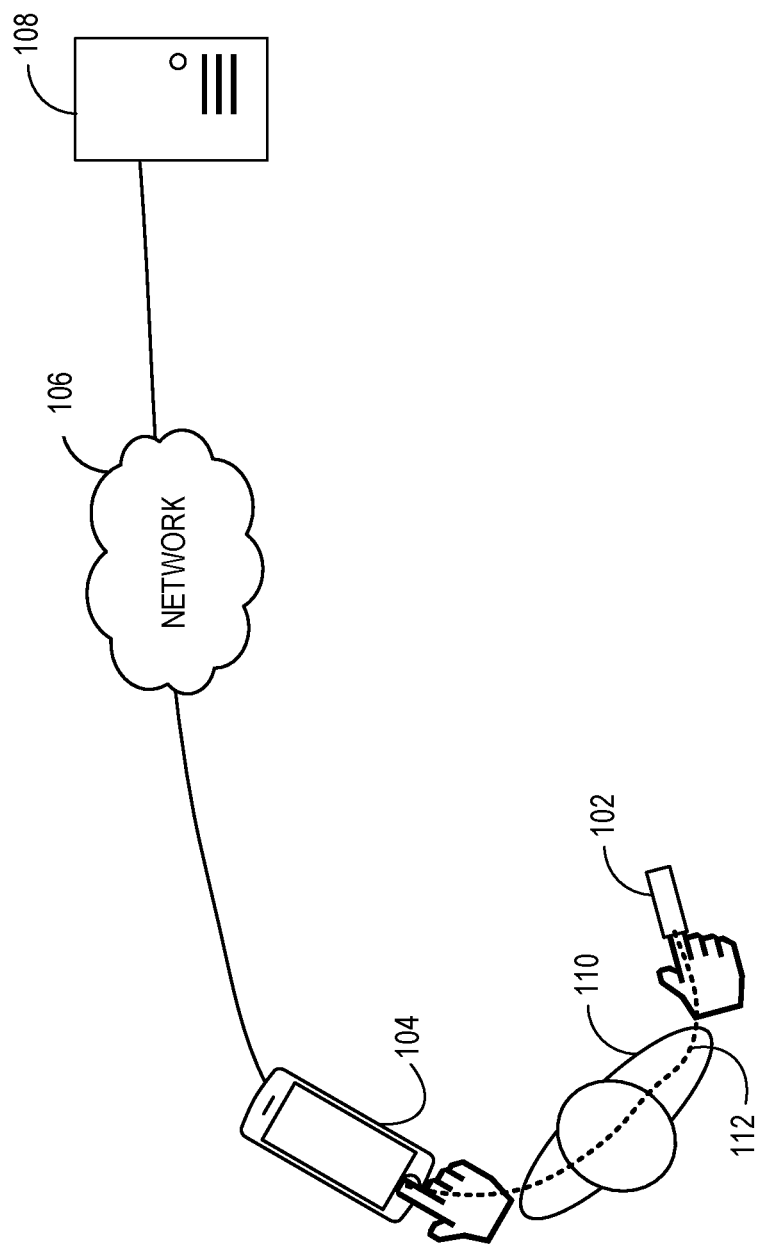
FIG. 1 illustrates a schematic diagram of a human body communication network, according to various examples.

FIG. 1 illustrates a schematic diagram 100 of an HBC network. Diagram 100 illustrates medical measurement device 102, computing device 104, external network 106, remote sever 108, user 110, and HBC transmission line 112. In an example, HBC transmission line 112 is not available unless user 110 maintains contact with medical measurement device 102 and computing device 104 at the same time.

Medical measurement device 102 may be a device that measures a user's vital signs or other medical data. Medical measurement device 102 may be, among other things, a quantifying-self sensor, like a weight-scale, a SpO2 device, or a blood pressure sensor. Additionally, medical measurement device 102 includes an HBC transceiver to communicate via HBC transmission line 112 with computing device 104. Medical measurement device 102 additionally may include two electrodes and the user 110 may make contact (e.g., using a finger) with both electrodes to establish HBC transmission line 112 in conjunction with the HBC transceiver.

Furthermore, medical measurement device 102 may include a storage device to store a private key. The private key may be used to digitally sign health measurement data taken by the medical measurement device 102. The storage device may also store a sensor identification (e.g., an alpha-numeric sequence of characters, a certificate, etc.). The medical measurement device 102 may include the sensor ID when transmitting any health measurement data or the ID may be transmitted separately.

Figure 2:
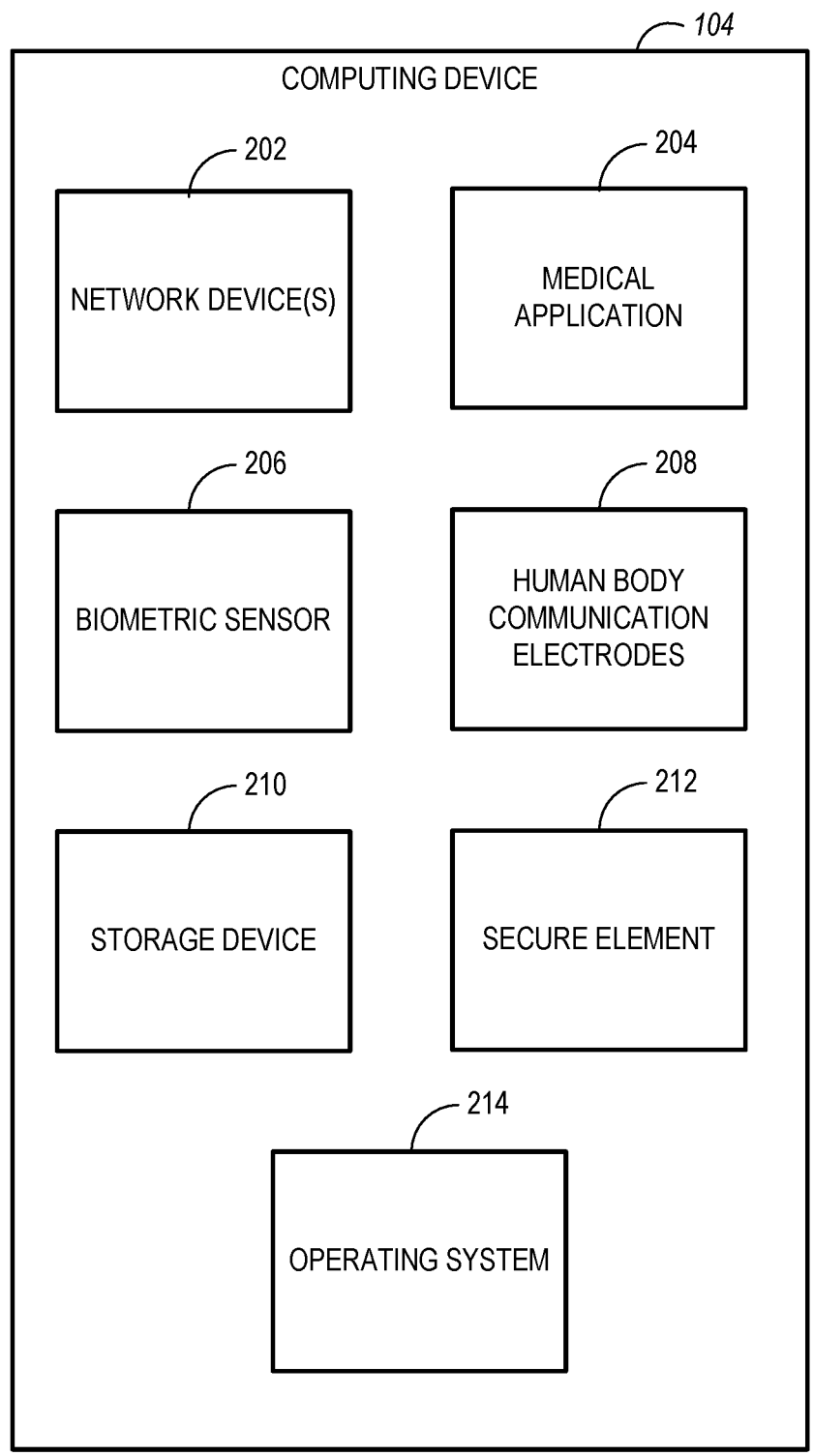
FIG. 2 illustrates a component diagram of a computing device, in various examples.

FIG. 2 illustrates a component diagram of a computing device 104, in various examples. Computing device 104 may include components such as network device 202, medical application 204, biometric sensor 206, human body communication electrodes 208, storage device 210, secure element 212, and operating system 214. While illustrated separately, the components may be related to each other or may function as a single component. For example, operating system 214 and medical application 204 may be stored on storage device 210.

Network device 202 may be used by computing device 104 to communicate with an external network 106 beyond the HBC network. External network 106 may include local-area networks (LAN), wide-area networks (WAN), wireless networks (e.g., 802.11 or cellular network), the Public Switched Telephone Network (PSTN) network, ad hoc networks, cellular, personal area networks besides HBC networks or peer-to-peer (e.g., Bluetooth®, Wi-Fi Direct), or other combinations or permutations of network protocols and network types. The network may include a single local area network (LAN) or wide-area network (WAN), or combinations of LANs or WANs, such as the Internet. Consequently, computing device 104 is able to connect to more than one type of network simultaneously. Computing device 104 may act as a relay device between remote sever 108 and medical measurement device 102 for health measurement data as discussed in more detail below.

In an example, the biometric sensor 206 is used by computing device 104 to authenticate user 110. Different types of biometric sensors may be used, but the examples herein discuss the use of fingerprint authentication. An application, such as medical application 204, may request that a user be authenticated while transmitting health measurement data. The request may be made using an API call to operating system 214.

To authenticate him/herself, the user may place a finger on biometric sensor 206. Biometric sensor 206 may capture fingerprint data optically or through a capacitance reader. The captured fingerprint data may be compared to preexisting fingerprint data—the user may previously have enrolled one or more fingerprints using biometric sensor 206—stored in in secure element 212. If operating system 214 determines there is a match, a message may be transmitted back to the requesting application. In an example, only operating system 214 has access to data stored in secure element 212.

Figure 3:
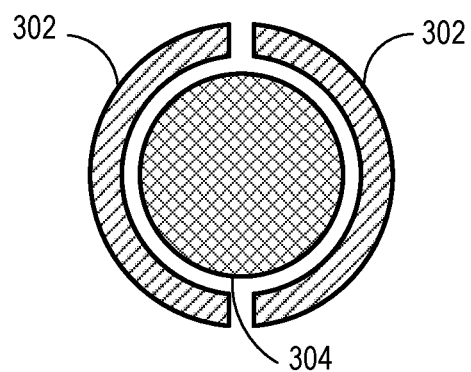
FIG. 3 and FIG. 4 illustrate arrangements of electrodes and a biometric sensor, according to various examples.
Figure 4:
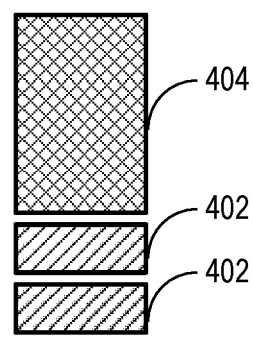

Human body communication electrodes 208 and biometric sensor 206 may be arranged to allow for a user to simultaneously maintain contract with both human body communication electrodes 208 and biometric sensor 206. FIG. 3 and FIG. 4 present example arrangements of electrodes and a biometric sensor. As seen in FIG. 3, electrodes 302 surround biometric sensor 304 where as in FIG. 4 electrodes 402 are located below biometric sensor 404. The arrangement of the electrodes and biometric sensor may be such that one person would not be able to make contact with both electrodes and a different person make contact with the biometric sensor at the same time.

Figure 5:
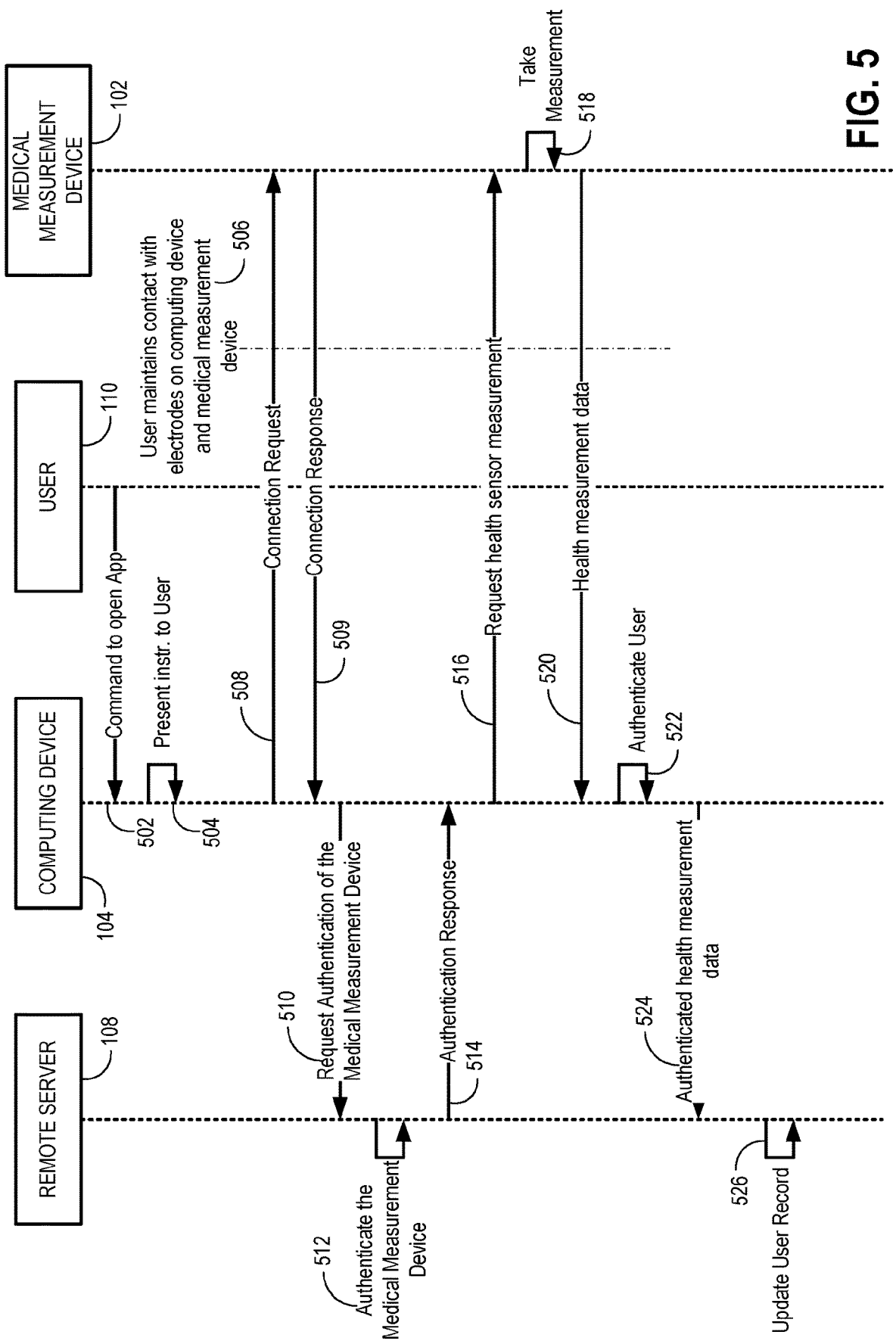
FIG. 5 illustrates a swim lane diagram, according to various examples.

FIG. 5 illustrates a swim lane diagram 500, according to various examples. Diagram 500 illustrates remote sever 108, computing device 104, user 110, and medical measurement device 102 and operations 502-526. Operations 502-526 may be used to retrieve health measurement data from medical measurement device 102, authenticate the health measurement data, and transmit it to remote sever 108.

In an example, a user 110 may begin by opening a medical application on computing device 104 (operation 502) such as medical application 204. The computing device 104 may access medical application 204 on storage device 210. Medical application 204 may be used with multiple medical measurement devices. In an example, medical application 204 is provided (e.g., through an app store or website) by remote sever 108. The medical application 204 may present a user interface through which a selection may be made for the type of medical device user 110 is currently using. This information may be used during the pairing process for configuration purposes as discussed below.

After selecting a medical measurement device 102, medical application 204 may present instructions on computing device 104 to have the user 110 place a finger simultaneously on the electrodes and biometric sensor of computing device 104 with one hand while simultaneously placing a finger on electrodes of medical measurement device 102 (operation 504) using the user's other hand. In further examples, the another body part may be used beyond a finger. For example, a person may use a toe to take a measurement.

Once the user 110 completes the instructions and maintains contact, computing device 104 may pair (e.g., establish a shared secret) with medical measurement device 102 over an HBC transmission line established through user 110. After pairing, data may be exchanged between computing device 104 and medical measurement device 102 without pairing again, even if a user 110 has since broken contact with electrodes on computing device 104 or medical measurement device 102. Depending on the capabilities of medical measurement device 102, pairing may be required each time data is exchanged. The pairing may be accomplished without the use of HBC transmission line 112. For example, medical measurement device 102 and computing device 104 may communicate using Bluetooth or Wi-Fi.

During or after the pairing process, computing device 104 may transmit configuration data from computing device 104 to medical measurement device 102. The configuration data may include information required by medical application 204 (e.g., the format of data, number of measurements, interval between measurements, etc.)

After pairing, computing device 104 may transmit a connection request to medical measurement device 102 at operation 508. At operation 509, medical measurement device 102 may send a connection response indicating medical measurement device 102 is able to send and receive data with computing device 104. In various examples, the response may also indicate the capabilities of medical measurement device 102. The capabilities may include the ability to digitally sign health measurement data or provide an identification of the sensor.

Although not illustrated, medical measurement device 102 may transmit an identification of a sensor on the medical measurement device 102 to computing device 104. Computing device 104 may transmit a request to remote sever 108 to authenticate the medical measurement device 102 at operation 510. The request may include the received sensor identification.

Remote server 108 may be a server administered by a health agency (e.g., hospital, clinic, etc.) to receive and process health measurement data from medical measurement devices. The server 108 may also be used to authenticate medical measurement devices. Remote server 108 may include more than one physical server, which may in turn be located in more than one geographic area. As part of establishing remote sever 108, a database (or multiple databases) may be maintained that include identifications of devices that have been authorized by the agency. If a particular device is not authorized, an identification of the sensor may still be maintained with a notation indicating the same. In some examples, the identification is a signed certificate.

Remote server 108 may query a database using the received sensor identification to authenticate the medical measurement device 102 at operation 512. If the sensor identification is in the database and marked as valid, an authentication response may be transmitted at operation 514. In some example, authentication of medical measurement device 102 is completed when health measurement data is received (e.g., during operation 524).

At operation 516, computing device 104 transmits a request to medical measurement device 102 via HBC transmission line 112 to take a health measurement of user 110. The request may include additional information to further ensure authenticity of any received data if medical measurement device 102 is more capable. The additional information may include the previously received sensor identification and a nonce.

In some examples, from operation 506-522 the user maintains contact with the electrodes and biometric sensor 206 on computing device 104 and the electrodes on medical measurement device 102. In other examples, user 110 may break contact after operation 509 and maintain contact again at operation 516 through operation 522.

At operation 518, in an example, medical measurement device 102 takes a health measurement of user 110. Multiple pieces of health measurement data may be taken as long as user 110 maintains contact with computing device 104 and medical measurement device 102. Different types of data may be collected according to the type of medical measurement device 102 and previously communicated configuration data.

Medical measurement device 102 may transmit the health measurement data to computing device 104 at operation 520. In some examples, medical measurement device 102 may transmit only the health measurement data. If the medical measurement device 102 is more capable, the health measurement data may be signed by the private key included in the medical measurement device 102. The signed data package may include the previously received nonce, the measurements, and the sensor identification. Signing may include calculating a hash of the data package and encrypting it using the private key. The encrypted hash may concatenated with the health measurement data (and nonce, etc.) may be considered signed data and be represented as "$Sign_{sensorpriv}$(nonce, health measurement data, sensor ID)."

At substantially the same time health measurement data is being collected, user 110 may be authenticated at operation 522. In some examples, the determination that user 110 is property authenticated may occur after the health measurement data is taken by medical measurement device 102; however, the information necessary for authentication (e.g., the information collected by biometric sensor 206) is collected before contact is broken with electrodes on either computing device 104 or medical measurement device 102. In this manner, the health measurement data may be unambiguously traced back to the same user the health measurement data is from.

To authenticate user 110, a call may be made to an API of operating system 214. Operating system 214 may respond if fingerprint data captured by biometric sensor 206 is considered a match with fingerprint data previously enrolled on computing device 104. Furthermore, a private key may be associated with the stored fingerprint data. The private key may be retrieved based on the user being authenticated.

In an example, at operation 524, the authenticated health measurement data is transmitted to remote server 108. The authenticated health measurement data may be signed using the retrieved private key. If the health measurement data was signed by medical measurement device 102 then the resulting package may look like: $Sign_{userpriv}(Sign_{sensorpriv}$(nonce, health measurement data, sensorID)). Other encryption methodologies may be used without departing from the scope of this disclosure. For example, a nonce may not be used.

At operation 526, remote sever 108 may update a record associated with user 110. The record may be medical history of user 110. Before the record is updated, remote sever 108 may verify that that the signed health measurement data belongs to an authenticated user. For example, a hash of the health measurement data (and any additional information) may be generated. A public key previously verified to be with associated user 110 may decode the signed health measurement data. If the calculated hash and decoded health measurement data match, the user may be considered authentic.

Although specific examples have been discussed with respect to a remote server and a medical record, the techniques described herein may be relevant to other uses as recognized by one of ordinary skill in the art. For example, the health measurement data may not be transmitted beyond computing device 104 and instead by stored in secure element 212. Similarly, health measurement data may be transmitted to family members.

Figure 6:
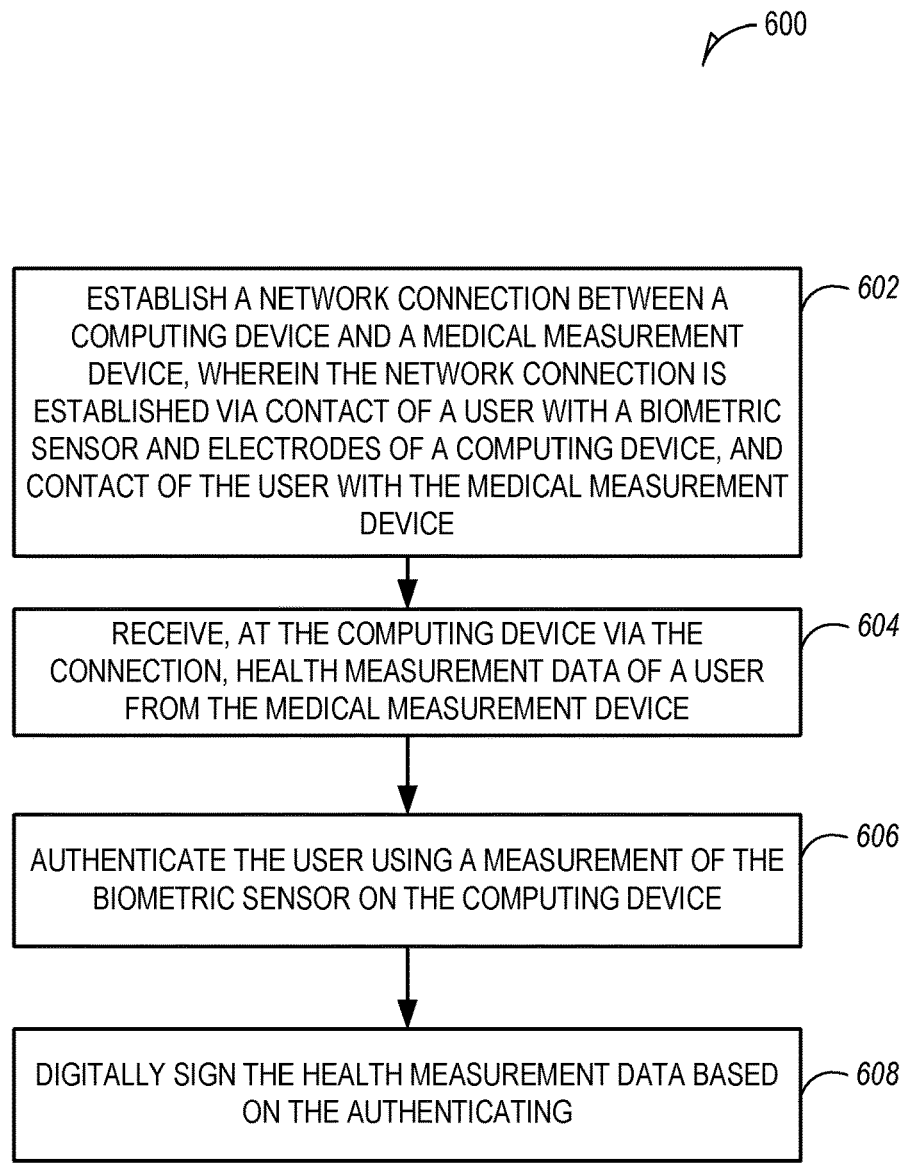
FIG. 6 illustrates a flowchart of a method for authenticating a health measurement taken from a medical measurement device, according to various examples.

FIG. 6 illustrates a flowchart of a method for authenticating a health measurement taken from a medical measurement device. The method may be performed by the components described herein. Computer-readable instructions may be stored on a non-transitory storage device, which when executed by at least one processor, may configure the at least one processor to perform the described method.

At operation 602, a network connection is established between a computing device and a medical measurement device. The network connection may be established via contact of a user with a biometric sensor of a computing device, contact with electrodes of the computing device, and contact of the user with the medical measurement device. The network connection may be a galvanic connection. The computing device may be paired with the medical measurement device over the network connection.

The user contact with computing device may be made using two electrodes on the computing device. The two electrodes may surround the biometric sensor. There may be a break between the two electrodes that surround the biometric sensor. The two electrodes may be adjacent to the biometric sensor. The biometric sensor may be a circle when the two electrodes surround the biometric sensor. The biometric sensor may be rectangle when the two electrodes are adjacent to the biometric sensor. Other shapes of electrodes and biometric sensors may also be used as long as these shapes force the user to make contact with the biometric sensor in order to touch both electrodes.

While contact is maintained with the electrodes and biometric sensor of the computing device and electrodes of the medical measurement device, health measurement data of a user may be received at the computing device from the medical measurement device at operation 604.

In an example, at operation 606, the user may be authenticated using a measurement (e.g., an optical image or capacitance reading) of the biometric sensor on the computing device.

The health measurement data may be digitally signed based on the authenticating at operation 608. The digitally signed health measurement data may be transmitted to a remote server over a second network connection. The second network connection may be a different type of connection than the network connection between the medical measurement device and computing device.

Digitally signing may include retrieving a private key associated with the user and digitally signing the measurement data using the private key. The health measurement data may also be signed using a private key of the medical measurement device.

In an example, an identification of the medical measurement device; may be received at the computing device from the medical measurement device. The identification of the medical measurement device may be transmitted to the remote server to determine that the medical measurement device is authentic.

EXAMPLE COMPUTER SYSTEM

Embodiments described herein may be implemented in one or a combination of hardware, firmware, and software. Embodiments may also be implemented as instructions stored on a machine-readable storage device, which may be read and executed by at least one processor to perform the operations described herein. A machine-readable storage device may include any non-transitory mechanism for storing information in a form readable by a machine (e.g., a computer). For example, a machine-readable storage device may include read-only memory (ROM), random-access memory (RAM), magnetic disk storage media, optical storage media, flash-memory devices, and other storage devices and media.

Examples, as described herein, may include, or may operate on, logic or a number of components, modules, or mechanisms. Modules may be hardware, software, or firmware communicatively coupled to one or more processors in order to carry out the operations described herein. Modules may hardware modules, and as such modules may be considered tangible entities capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a machine-readable medium. In an example, the software, when executed by the underlying hardware of the module, causes the hardware to perform the specified operations. Accordingly, the term hardware module is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software; the general-purpose hardware processor may be configured as respective different modules at different times. Software may accordingly configure a hardware processor, for example, to constitute a particular module at one instance of time and to constitute a different module at a different instance of time. Modules may also be software or firmware modules, which operate to perform the methodologies described herein.

Figure 7:
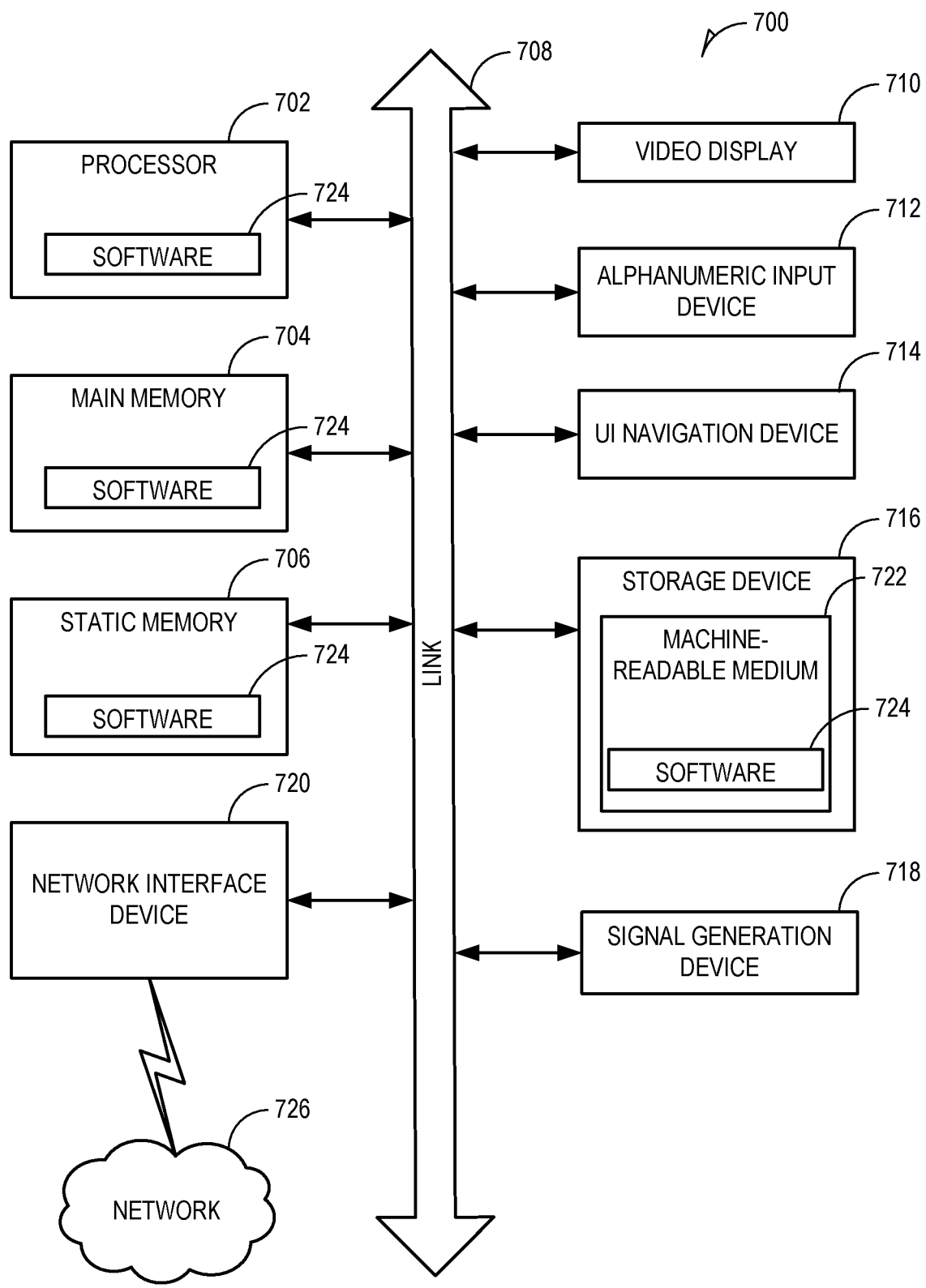
FIG. 7 is a block diagram illustrating an example machine upon which any one or more of the techniques (e.g., methodologies) discussed herein may be performed, according to an example embodiment.

FIG. 7 is a block diagram illustrating a machine in the example form of a computer system 700, within which a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a wearable device, personal computer (PC), a tablet PC, a hybrid tablet, a personal digital assistant (PDA), a mobile telephone, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by a processor (e.g., a computer) to individually or jointly execute instructions to perform any one or more of the methodologies discussed herein.

Example computer system 700 includes at least one processor 702 (e.g., a central processing unit (CPU), a graphics processing unit (GPU) or both, processor cores, compute nodes, etc.), a main memory 704 and a static memory 706, which communicate with each other via a link 708 (e.g., bus). The computer system 700 may further include a video display unit 710, an alphanumeric input device 712 (e.g., a keyboard), and a user interface (UI) navigation device 714 (e.g., a mouse). In one embodiment, the video display unit 710, input device 712 and UI navigation device 714 are incorporated into a touch screen display. The computer system 700 may additionally include a storage device 716 (e.g., a drive unit), a signal generation device 718 (e.g., a speaker), a network interface device 720, and one or more sensors (not shown), such as a global positioning system (GPS) sensor, compass, accelerometer, or other sensor.

The storage device 716 includes a machine-readable medium 722 on which is stored one or more sets of data structures and instructions 724 (e.g., software) embodying or utilized by any one or more of the methodologies or functions described herein. The instructions 724 may also reside, completely or at least partially, within the main memory 704, static memory 706, and/or within the processor 702 during execution thereof by the computer system 700, with the main memory 704, static memory 706, and the processor 702 also constituting machine-readable media.

While the machine-readable medium 722 is illustrated in an example embodiment to be a single medium, the term "machine-readable medium" may include a single medium or multiple media (e.g., a centralized or distributed database, and/or associated caches and servers) that store the one or more instructions 724. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 724 may further be transmitted or received over a communications network 726 using a transmission medium via the network interface device 720 utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., Wi-Fi, 7G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

Example 1 is a system for authenticating a health measurement taken from a medical measurement device, the system comprising: at least one processor; a biometric sensor; a plurality of electrodes; a storage device comprising instructions, which when executed by the at least one processor, configure the at least one processor to: establish a network connection between the system and a medical measurement device, wherein the network connection is established via contact of a user with the plurality of electrodes of the system and contact of the user with electrodes of the medical measurement device; while user contact is maintained with the plurality of electrodes of the system and the electrodes of the medical measurement device: receive, via the network connection, health measurement data of the user from the medical measurement device; and authenticate the user using a measurement of the biometric sensor; and digitally sign the health measurement data based on the authenticating.

In Example 2, the subject matter of Example 1 optionally includes, wherein the at least one processor is further configured to: transmit the digitally signed health measurement data to a remote server from the system over a second network connection, wherein the second network connection is a different type of connection than the network connection between the medical measurement device and the system.

In Example 3, the subject matter of any one or more of Examples 1-2 optionally include, wherein the user contact with the system is made using two electrodes on the computing device.

In Example 4, the subject matter of Example 3 optionally includes, wherein the two electrodes are adjacent to the biometric sensor.

In Example 5, the subject matter of any one or more of Examples 3-4 optionally include, wherein the two electrodes surround the biometric sensor.

In Example 6, the subject matter of any one or more of Examples 1-5 optionally include, wherein the network connection is a galvanic connection.

In Example 7, the subject matter of any one or more of Examples 1-6 optionally include, wherein the at least one processor is further configured to: pairing the computing device with the medical measurement device over the network connection.

In Example 8, the subject matter of any one or more of Examples 1-7 optionally include, wherein to digitally sign the health measurement data, the at least one processor is configured to: retrieve a private key associated with the user; and digitally sign the health measurement data using the private key.

In Example 9, the subject matter of any one or more of Examples 1-8 optionally include, wherein the at least one processor is further configured to: receive, over the network connection, an identification of the medical measurement device; and transmit the identification of the medical measurement device to a remote server to determine that the medical measurement device is authentic.

In Example 10, the subject matter of any one or more of Examples 1-9 optionally include, wherein the health measurement data is digitally signed using a private key of the medical measurement device.

Example 11 is a method of authenticating a health measurement taken from a medical measurement device, the method comprising: establishing a network connection between a computing device and a medical measurement device, wherein the network connection is established via contact of a user with electrodes of the computing device and contact of the user with electrodes of the medical measurement device; while user contact is maintained with the electrodes of the computing device, the electrodes of the medical measurement device, and a biometric sensor of the computing device: receiving, at the computing device via the network connection, health measurement data of the user from the medical measurement device; and authenticating the user using a measurement of the biometric sensor of the computing device; and digitally signing the health measurement data based on the authenticating.

In Example 12, the subject matter of Example 11 optionally includes, further comprising: transmitting the digitally signed health measurement data to a remote server from the computing device over a second network connection, wherein the second network connection is a different type of connection than the network connection between the medical measurement device and computing device.

In Example 13, the subject matter of any one or more of Examples 11-12 optionally include, wherein the user contact with the computing device is made using two electrodes on the computing device.

In Example 14, the subject matter of Example 13 optionally includes, wherein the two electrodes are adjacent to the biometric sensor.

In Example 15, the subject matter of any one or more of Examples 13-14 optionally include, wherein the two electrodes surround the biometric sensor.

In Example 16, the subject matter of any one or more of Examples 11-15 optionally include, wherein the network connection is a galvanic connection.

In Example 17, the subject matter of any one or more of Examples 11-16 optionally include, further comprising: pairing the computing device with the medical measurement device over the network connection.

In Example 18, the subject matter of any one or more of Examples 11-17 optionally include, wherein digitally signing the health measurement data comprises: retrieving a private key associated with the user; and digitally signing the health measurement data using the private key.

In Example 19, the subject matter of any one or more of Examples 11-18 optionally include, further comprising: receiving, over the network connection, an identification of the medical measurement device; and transmitting the identification of the medical measurement device to a remote server to determine that the medical measurement device is authentic.

In Example 20, the subject matter of any one or more of Examples 11-19 optionally include, wherein the health measurement data is digitally signed using a private key of the medical measurement device.

Example 21 is at least one machine-readable medium including instructions, which when executed by a machine, cause the machine to perform operations of any of the methods of Examples 11-20.

Example 22 is an apparatus comprising means for performing any of the methods of Examples 11-20.

Example 23 is an apparatus of authenticating a health measurement taken from a medical measurement device, the apparatus comprising: means for establishing a network connection between a computing device and a medical measurement device, wherein the network connection is established via contact of a user with electrodes of the computing device and contact of the user with electrodes of the medical measurement device; while user contact is maintained with the electrodes of the computing device, the electrodes of the medical measurement device, and a biometric sensor of the computing device: means for receiving, at the computing device via the network connection, health measurement data of the user from the medical measurement device; and means for authenticating the user using a measurement of the biometric sensor of the computing device; and means for digitally signing the health measurement data based on the authenticating.

In Example 24, the subject matter of Example 23 optionally includes, further comprising: means for transmitting the digitally signed health measurement data to a remote server from the computing device over a second network connection, wherein the second network connection is a different type of connection than the network connection between the medical measurement device and computing device.

In Example 25, the subject matter of any one or more of Examples 23-24 optionally include, wherein the user contact with the computing device is made using two electrodes on the computing device.

In Example 26, the subject matter of Example 25 optionally includes, wherein the two electrodes are adjacent to the biometric sensor.

In Example 27, the subject matter of any one or more of Examples 25-26 optionally include, wherein the two electrodes surround the biometric sensor.

In Example 28, the subject matter of any one or more of Examples 23-27 optionally include, wherein the network connection is a galvanic connection.

In Example 29, the subject matter of any one or more of Examples 23-28 optionally include, further comprising: means for pairing the computing device with the medical measurement device over the network connection.

In Example 30, the subject matter of any one or more of Examples 23-29 optionally include, wherein digitally signing the health measurement data comprises: means for retrieving a private key associated with the user; and means for digitally signing the health measurement data using the private key.

In Example 31, the subject matter of any one or more of Examples 23-30 optionally include, further comprising: means for receiving, over the network connection, an identification of the medical measurement device; and means for transmitting the identification of the medical measurement device to a remote server to determine that the medical measurement device is authentic.

Example 32 is a system that enables a user to establish a network connection between the system and a medical measurement device based on user contact with the system and the medical measurement device, and while user contact is maintained with the system and medical measurement device, the system configured to: receive, via the network connection, health measurement data of the user from the medical measurement device; and authenticate the user using a measurement of a biometric sensor of the sensor; and digitally sign the health measurement data based on the authenticating.

In Example 33, the subject matter of Example 32 optionally includes, wherein the network connection is a galvanic connection.

Example 34 is then system of Example 33, wherein the system is further configured to pair the system with the medical measurement device over the network connection.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, also contemplated are examples that include the elements shown or described. Moreover, also contemplate are examples using any combination or permutation of those elements shown or described (or one or more aspects thereof), either with respect to a particular example (or one or more aspects thereof), or with respect to other examples (or one or more aspects thereof) shown or described herein.

What is claimed is:

1. A system for authenticating a health measurement taken from a medical measurement device, the system comprising:
   at least one processor;
   a biometric sensor;
   a plurality of electrodes;
   a storage device comprising instructions, which when executed by the at least one processor, configure the at least one processor to:
      establish a network connection between the system and a medical measurement device, the medical measurement device distinct and independent from the system, wherein the network connection uses a body of a user as a transmission medium to form the network connection via a first contact between the user with the plurality of electrodes of the system and a second contact between the user with electrodes of the medical measurement device and wherein the first contact and the second contact are at separate and distinct locations on the user;
      receive, over the network connection, sensor identifications for the electrodes of the medical measurement device;
      transmit the sensor identifications to a remote authentication server;
      receive an authentication of the medical measurement device from the remote authentication server;
      while user contact and the network connection using the body as the transmission medium is maintained with the plurality of electrodes of the system and the electrodes of the medical measurement device:
         transmit a request for health measurement data, via the network connection, including the sensor identifications;
         receive, via the network connection, the health measurement data of the user and the sensor identifications from the medical measurement device; and
         authenticate the user using a measurement of the biometric sensor; and
      digitally sign the health measurement data based on the authenticating.

2. The system of claim 1, wherein the at least one processor is further configured to:
   transmit the digitally signed health measurement data to a remote server from the system over a second network connection, wherein the second network connection is a different type of connection than the network connection between the medical measurement device and the system.

3. The system of claim 1, wherein the user contact with the system is made using two electrodes on the system.

4. The system of claim 3, wherein the two electrodes are adjacent to the biometric sensor.

5. The system of claim 3, wherein the two electrodes surround the biometric sensor.

6. The system of claim 1, wherein the network connection is a galvanic connection.

7. The system of claim 1, wherein the at least one processor is further configured to:
pairing the system with the medical measurement device over the network connection.

8. The system of claim 1, wherein to digitally sign the health measurement data, the at least one processor is configured to:
retrieve a private key associated with the user; and
digitally sign the health measurement data using the private key.

9. The system of claim 1, wherein the health measurement data is digitally signed using a private key of the medical measurement device.

10. A method of authenticating a health measurement taken from a medical measurement device, the method comprising:
establishing a network connection between a computing device and a medical measurement device, the medical measurement device distinct and independent from the system, wherein the network connection uses a body of a user as a transmission medium to form the network connection via a first contact between the user with electrodes of the computing device and a second contact between the user with electrodes of the medical measurement device and wherein the first contact and the second contact are at separate and distinct locations on the user;
receiving, over the network connection, sensor identifications for the electrodes of the medical measurement device;
transmitting the sensor identifications to a remote authentication server;
receiving an authentication of the medical measurement device from the remote authentication server;
while user contact and the network connection using the body as the transmission medium is maintained with the electrodes of the computing device, the electrodes of the medical measurement device, and a biometric sensor of the computing device:
transmitting a request for health measurement data, via the network connection, including the sensor identifications;
receiving, at the computing device via the network connection, health measurement data of the user and sensor identifications from the medical measurement device; and
authenticating the user using a measurement of the biometric sensor of the computing device; and
digitally signing the health measurement data based on the authenticating.

11. The method of claim 10, further comprising:
transmitting the digitally signed health measurement data to a remote server from the computing device over a second network connection, wherein the second network connection is a different type of connection than the network connection between the medical measurement device and computing device.

12. The method of claim 10, wherein the user contact with the computing device is made using two electrodes on the computing device.

13. The method of claim 12, wherein the two electrodes are adjacent to the biometric sensor.

14. The method of claim 12, wherein the two electrodes surround the biometric sensor.

15. At least one non-transitory machine-readable medium including instructions, which when executed by a machine, cause the machine to perform operations:
establishing a network connection between a computing device and a medical measurement device, the medical measurement device distinct and independent from the system, wherein the network connection uses a body of a user as a transmission medium to form the network connection via a first contact between the user with electrodes of the computing device and a second contact between the user with electrodes of the medical measurement device and wherein the first contact and the second contact are at separate and distinct locations on the user;
receiving, over the network connection, sensor identifications for the electrodes of the medical measurement device;
transmitting the sensor identifications to a remote authentication server;
receiving an authentication of the medical measurement device from the remote authentication server;
while user contact and the network connection using the body as the transmission medium is maintained with the electrodes of the computing device, the electrodes of the medical measurement device, and a biometric sensor of the computing device:
transmitting a request for health measurement data, via the network connection, including the sensor identifications;
receiving, at the computing device via the network connection, health measurement data of the user and the sensor identifications from the medical measurement device; and
authenticating the user using a measurement of the biometric sensor of the computing device; and
digitally signing the health measurement data based on the authenticating.

16. The non-transitory machine-readable medium of claim 15, the operations further comprising:
transmitting the digitally signed health measurement data to a remote server from the computing device over a second network connection, wherein the second network connection is a different type of connection than the network connection between the medical measurement device and computing device.

17. The non-transitory machine-readable medium of claim 15, wherein the user contact with the computing device is made using two electrodes on the computing device.

18. The non-transitory machine-readable medium of claim 17, wherein the two electrodes are adjacent to the biometric sensor.

19. The non-transitory machine-readable medium of claim 17, wherein the two electrodes surround the biometric sensor.

20. The non-transitory machine-readable medium of claim 15, wherein the network connection is a galvanic connection.

21. The non-transitory machine-readable medium of claim 15, further comprising pairing the computing device with the medical measurement device over the network connection.

22. The non-transitory machine-readable medium of claim 15, wherein digitally signing the health measurement data, includes operations further comprising:
 retrieving a private key associated with the user; and
 digitally signing the health measurement data using the private key.

* * * * *